United States Patent [19]

Schlingmann et al.

[11] Patent Number: 5,334,535
[45] Date of Patent: Aug. 2, 1994

[54] PROCESS FOR THE PREPARATION OF OPTICALLY PURE DIASTEREOISOMERS OF TETRAHYDROFOLATE COMPOUNDS USING 10-FORMYLTETRAHYDROFOLATE SYNTHETASE FROM CLOSTRIDIUM

[75] Inventors: Gerhard Schlingmann, Hilburn, N.Y.; Stuart A. Rosenfeld, Alameda, Calif.

[73] Assignee: American Cyanamid Company, Wayne, N.J.

[21] Appl. No.: 947,641

[22] Filed: Sep. 18, 1992

Related U.S. Application Data

[63] Continuation of Ser. No. 449,662, Dec. 11, 1989, abandoned.

[51] Int. Cl.$^5$ .................. C12P 41/00; C12P 13/14
[52] U.S. Cl. .................. 435/280; 435/110; 435/842
[58] Field of Search .................. 435/280, 110, 842

[56] References Cited

U.S. PATENT DOCUMENTS 4,500,711 2/1985 Wisowaty .................. 544/258
4,746,662 5/1988 Kerwar .................. 514/258

FOREIGN PATENT DOCUMENTS 0266042 4/1988 European Pat. Off. .
7332120 9/1969 Japan .
2003869 3/1979 United Kingdom .

OTHER PUBLICATIONS

Rebello T., Anal Biochem 166:55–64 (1987).
Gounelle J. C., et al., Anal Biochem. 176:406–411 (1989).
Fawaz, M. et al., Ann. Pharm. Fr. 46:121–128 (1988).
Joyce B. K., JBC 241:5725–5731 (1966).
Temple et al., J. Med. Chem. 22:731–734 (79).
Buttlaire, Methods in Enzymology 66: 585–599 (80).
Temple et al., J. Chromatography 140: 114—117 (77).
Moran et al., Anal Biochem 122:70–78 (82).
Remington's Pharmaceutical Services 1985 p. 1023.
Physician's Desk Reference 43rd Edition, p. 1124.
C. Temple et al, Cancer Treatment Reports, 65 pp. 1117–1119 (1981).
Biochemistry, vol. 28, No. 12, 1989, pp. 5136–5145 Mejillano et al, "Formation and Utilization."
R. P. Leary et al, Biochemical and Biophysical Research Communications, 56, 484–488 (1974).
V. F. Scott et al, Biochemical and Biophysical Research Communications, 14, 523–526 (1964).
G. K. Smith et al, Biochemistry 20, 4034–4036 (1981).
D. B. Cosulich et al, Journal American Chemical Society, 74, 4215–4216.
J. Feeney et al, Biochemistry, 20, 1837–1842 (1981).
L. Rees et al, Tetrahedron, 42, 117–136 (1986).
L. Rees et al, J. Chemical Society Chemical Communications, 470–472 (1987).
C. Temple et al, Journal Medical Chemistry, 25, 161–166 (1982).
J. A. Blair et al, Analytical Biochemistry, 34, 376–381 (1970).

*Primary Examiner*—Douglas W. Robinson
*Assistant Examiner*—S. Saucier
*Attorney, Agent, or Firm*—Thomas Szatkowski

[57] ABSTRACT

A process for the preparation of optically pure diastereoisomers of tetrahydrofolate compounds is described, comprising the conversion, for example, of only the 5,6S,7,8-tetrahydrofolic acid component of a racemic mixture of 5,6,7,8-tetrahydrofolic acid to 10-formyl-5,6S,7,8-tetrahydrofolic acid in the presence of a formyl tetrahydrofolate synthetase, followed by cyclizing, hydrolyzing and derivatizing. The process is also useful to make a desired substantially pure (6R or 6S) enantiomer of a derivative of (radiolabeled) tetrahydrofolic acid or a salt or ester thereof.

1 Claim, No Drawings

PROCESS FOR THE PREPARATION OF OPTICALLY PURE DIASTEREOISOMERS OF TETRAHYDROFOLATE COMPOUNDS USING 10-FORMYLTETRAHYDROFOLATE SYNTHETASE FROM CLOSTRIDIUM

This is a continuation of co-pending application Ser. No. 07/449,662, filed on Dec. 11, 1989, now abandoned.

The present invention relates to a new process for the preparation of optically pure diastereoisomers of tetrahydrofolate compounds comprising converting only the 5,6S,7,8-tetrahydrofolic acid component of a racemic mixture of 5,6,7,8-tetrahydrofolic acid to 10-formyl-5,6S,7,8-tetrahydrofolic acid in the presence of a bacterially derived formyl tetrahydrofolate synthetase.

BACKGROUND OF THE INVENTION

Leucovorin and its salts are known to be pharmaceutically effective. See, Remington's Pharmaceutical Services, Mack Publishing Co., Easton, PA 1985 (Remington's) p. 1023. Kerwar et al., U.S. Pat. No. 4,746,662 disclose that the antiarthritic efficacy of methotrexate can be potentiated by injection of an aqueous solution of leucovorin or its salts. EPO Patent Publication No. 0,266,042, May 4, 1988, describes using pure leucovorin isomers to manufacture medicaments for methotrexate rescue, for treatment of colorectal cancer in combination with 5-fluorouracil, and for treating folate deficiency. In U.S. Pat. No. 4,500,711, Wisowaty et al., describe the purification of leucovorin and its salts.

Leucovorin is normally administered in the form of salts such as alkaline metal and alkaline earth metal salts, such as the calcium salt of leucovorin, with the 1-isomer being preferred.

The compound N-(((2-amino-5-formyl-3,4,5,6,7,8-hexahydro-4-oxo-6-pteridinyl)methyl)amino)benzoyl)-L-glutamic acid, calcium salt (1:1), pentahydrate, (Leucovorin Calcium USP) is sold commercially as the calcium salt of a 1:1 mixture of formulae (Ia and Ib) for which the compounds have the (R) and (S) stereochemistry respectively at C-6.

It is used principally as an antidote for folic acid antagonists such as methotrexate, which blocks the conversion of dihydrofolic acid to tetrahydrofolic acid. Leucovorin salts are formulated in water for injection with suitable preservatives, as described under Leucovorin Calcium Injection in the Physician's Desk Reference, Forty-third Edition, Medical Economics Company, Oradell, NJ 1989 (PDR 43rd Ed.) p. 1124.

The pharmacokinetic behavior of the two isomers differs in that the (S)-isomer IIb) is selectively absorbed from the gastrointestinal tract and has a shorter plasma half-life relative to the (R)-isomer (Ia).

The naturally occurring isomer Ib, which is the 6S diastereoisomer, has been reported (C. Temple, Jr., J. P. Rose, W. R. Laster, and J. A. Montgomery, Cancer Treatment Reports, 65, 1117–1119 (1981)) to be important for rescue therapy by virtue of its effectiveness at restoring one-carbon metabolism.

A report (R. P. Leary, Y. Gaumont, and R. L. Kisliuk, Biochem. and Biophys. Res. Commun., 56, 484–488 (1974)) that thymidylate synthesis from L. casei is inhibited by the non-natural diastereoisomer of 5,10methylene tetrahydrofolate and a report (V. F. Scott and K. O. Donaldson, Biochem. and Biophys. Res. Commun., 14, 523–526 (1964)) that 5,10-methylene tetrahydrofolate dehydrogenase from $E.\ coli$ is also inhibited by the same diastereoisomer coupled with the observation (G. K. Smith, P. A. Benkovic, and S. J. Benkovic, Biochem., 20, 4034–4036 (1981)) that the same diastereoisomer of 10-formyltetrahydrofolate is a potent competitive inhibitor of Glycinamide ribonucleotide formyltransferase (GAR) from chicken liver points to the inhibition of both pyrimidine and purine biosynthesis and thus of DNA biosynthesis by the non-natural diastereoisomers of one-carbon derivatives of tetrahydrofolate. Therefore, the non-natural forms cannot be considered as biologically inert. If such inhibition is present in mammalian systems, then a potential clinical requirement for only the natural (6S) form of tetrahydrofolates, especially leucovorin, exists.

The diastereoisomeric components Ia and Ib have been separated (D. B. Cosulich, J. M. Smith, Jr. and H. P. Proglist, J. Am. Chem. Soc., 74, 4215 (1953)) by fractional crystallization and by chromatography (J. Feeney, B. Birdsall, J. P. Albrand, G. C. K. Roberts, A. S. Bungen, P. A. Charlton and D. W. Young, Biochem., 20, 1837 (1981)). A stereospecific reduction of dihydrofolate catalyzed by dihydrofolate reductase has been reported (L. Rees, E. Valente, C. J. Suckling and H. C. S. Wood, Tetrahedron, 42, 117 (1986)) to afford the 6(S)-isomer stereospecifically.

A paper by L. Rees, E. Valente, C. Suckling and H. C. S. Wood, Tetrahedron, 42, 117–136 (1986) describes the synthesis of chiral derivatives of tetrahydrofolate, including leucovorin. This system required the use of

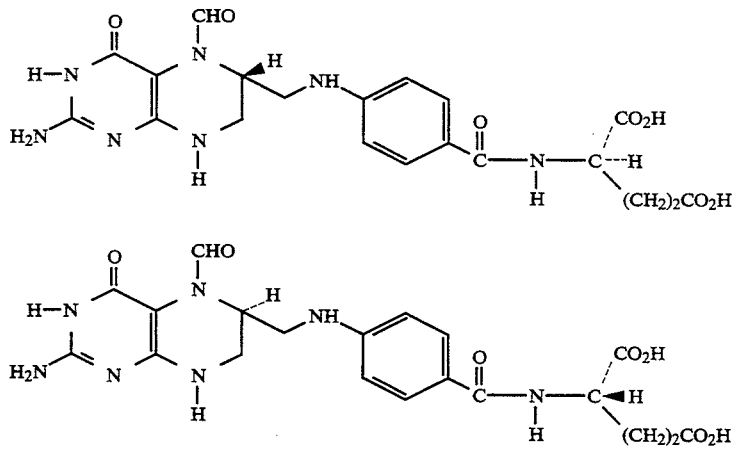

dihydrofolate reductase from E. coli and an extensive and expensive recycling of reducing cofactor NADPH. Another paper by L. Rees, C. J. Suckling and H. C. S. Wood, J. Chem. Soc. Chem. Commun. 470, (1987) (European Patent Application 0 266 042 A2) describes the acylation of 6(R,S)-tetrahydrofolate with (—)-menthyl chloroformate to give N-5 derivatives as a diastereoisomeric mixture which were separated by fractional precipitation. Subsequent treatment of each diastereoisomer with formic acid and hydrogen bromide in acetic acid followed by hydrolysis gave each diastereoisomer of 5-formyltetrahydrofolate.

It has now been found that the optically pure diastereoisomers of tetrahydrofolate compounds can be produced easier in accordance with this invention. This process has a major advantage over previously published or patented procedures in that it is surprisingly simple, because the key step requires only the use of one enzyme, tetrahydrofolate formylase, otherwise called formate activating enzyme or formyltetrahydrofolate synthetase (FTHFS), which also selectively adds the required formyl group to only the 6S diastereoisomer when using a racemic mixture of 5,6(R,S),7,8-tetrahydrofolic acid (IIa,b). Further, the utilization of this enzyme has a distinct advantage over the use of the enzyme dihydrofolate reductase in that an extensive regeneration system for cofactors does not have to be employed.

Tetrahydrofolate formylase can be elaborated by *Micrococcus aerogenes, Clostridium cylindrosporum, Clostridium acidi-urici, Clostridium thermoaceticum,* and by other microorganisms, plants and animals. D. H. Butlaire, Methods In Enzymology, 66, 585-599 -(1980).

By using radiolabeled ammonium formate or any other, including in situ made, radiolabeled formic acid salts or derivatives in the enzymatic formylation, labeled (IIIb) can be obtained and converted to labeled (IVb) or labeled (Ib). With the aid of the enzyme 5,10-methylenetetrahydrofolate dehydrogenase any of the radiolabeled, formyl group carrying 5,6S,7,8-tetrahydro-folates (Ib,IIIb, or IVb), preferably (IVb), can be transformed to labeled 5,10-methylene-5,6S,7,8-tetrahydro-folic acid which in turn, under the action of the enzyme 5,10-methylenetetrahydrofolate reductase can be converted to radiolabeled 5-methyl-5,6S,7,8-tetrahydrofolic acid. Thus, radiolabeled (Ib) generated by the application of this invention is a useful compound for the production of radiolabeled 5,6S,7,B-tetrahydrofolic acid derivatives.

The invented process also unexpectedly allows for the isolation of 5,6R,7,8-tetrahydrofolic acid (IIa) which is not formylated by the enzyme. Isolated (IIa) can then be sold as such (commercialized as a rare compound) or serve as the starting material for the production of, for example, 5-formyl-5,6R,7,8-tetrahydrofolic acid (Ia) in an analogy to a procedure described by R. G. Moran and P. D. Colman, Anal. Biochem. 122, 70–78 (1982) using formic acid with or without the water-soluble carbodiimide, 1-ethyl-3-(3 -dimethyl-aminopropyl) carbodiimide. Preferable, however, is the isolation of (IIa) after the conversion of (IIIb) to (IVb) and/or (Ib) has been completed. This allows for an easier separation of the components by reverse-phase chromatography, for example. Also, (IIa) can be modified in the presence of (IVb) and/or (Ib), since the 5-position of (IIa) is still reactive whereas that of (IVb) or (Ib) is not, to produce derivatized (IIa), for example 5-carboxymenthyl-5,6R,7,8-tetrahydrofolic acid, which can be separated from (IVb) or (Ib) in a simple adsorption step.

Furthermore, separated (IIa) can be reacted as reported by C. Temple, Jr. , L. L. Bennett, Jr. , J. D. Rose, R. D. Elliott, J. A. Montgomery and J. H. Mangum, J. Med. Chem., 25, 161–166 (1982) to prepare various 5- and 10- substituted, 5,10-disubstituted , and 5,10-bridgesubstituted 5,6R,7,8-tetrahydrofolic acid derivatives. In particular, 5-methyl-5,6R,7,8-tetrahydrofolate can be synthesized from (IIa) with formaldehyde and sodium borohydride under basic conditions as described in a method by J. A. Blair and K. J. Saunders, Anal. Biochem. , 34, 376 (1970). Alkylation of (IIa) with dimethylsulfate in N,N-dimethylacetamide at 55° C. is achieved by using a method·described in Japanese patent 73 32,120 (1973); Chem. Abst. , 80, 2792X (1974) .

By substituting formic acid or the alkylating agents in the above indicated reactions with radiolabeled formic acid or derivatives thereof or radioactive alkylating agents, radiolabeled 5,6R,7,8-tetrahydrofolic acid derivatives will be obtained.

in accordance with this invention, both radio-labeled 5,6S,7,8-tetrahydrofolic acid derivatives and radiolabeled 5,6R,7,8-tetrahydrofolic acid derivatives and their salts can be produced separately, which are useful compounds for testing, for example studying enzymatic mechanisms.

SUMMARY OF THE INVENTION

According to the present invention, there is provided a process for the preparation of a desired substantially pure (6R or 6S) diastereoisomer of a derivative of tetrahydrofolic acid or a salt or an ester thereof, which process comprises the steps of:

(a) enzymatically formylating the 6S form of a mixture of 6R and 6S diastereoisomers of tetrahydrofolic acid or of a substituted tetrahydrofolic acid or a salt or an ester thereof so as to form a mixture comprising 10-formyl-5,6S,7,8-tetrahydrofolic acid or a salt or an ester thereof; unreacted 5,6S,7,8-tetrahydrofolic acid or a salt or an ester thereof if present; unreacted 5,6R,7,8-tetrahydrofolic acid or a salt or an ester thereof; and either (b)(1) separating 10-formyl-5,6S,7,8-tetrahydrofolic acid or a salt or an ester thereof from 5,6R, 7,8-tetrahydrofolic acid or a salt or an ester thereof and thereafter cyclizing and hydrolyzing said 10-formyl5,6S,7,8-tetrahydrofolic acid or a salt or an ester thereof so as to form 5,10-methenyl-5,6S,7,8-tetrahydrofolic acid, or 5-formyl-5,6S,7,8-tetrahydrofolic acid or salts or esters thereof, or both of the foregoing; or (2) cyclizing and hydrolyzing said 10-formyl-5,6S,7,8-tetrahydrofolic acid or a salt or an ester thereof so as to form 5,10-methenyl-5,6S,7,8-tetrahydrofolic acid, or 5-formyl-5,6S,7,8-tetrahydrofolic acid or salts or esters thereof, or both of the foregoing, in the presence of 5,6R,7,8-tetranydrofolic acid or a salt or an ester thereof; and thereafter either (i) derivatizing 5,6R,7,8-tetrahydrofolic acid or a salt or an ester thereof so as to form 5-substituted 5,6R,7,8-tetrahydrofolic acid or a salt or an ester thereof and then separating the components, or alternatively (ii) separating any 5,10-methenyl-5,6S,7, 8-tetrahydrofolic acid and any 5-formyl-5,6S,7,8-tetrahydrofolic acid or salts or esters thereof from 5,6R,7, 8-tetrahydrofolic acid or a salt or an ester thereof; and after separation, if desired (3) chemically formylating, cyclizing, and hydrolyzing said unreacted 5,6R,7,8-tetrahydrofolic acid or a salt or an ester thereof so as to produce 5-formyl-5,6R,7,8-tetrahydrofolic acid or a salt or an ester thereof, or, alternatively, derivatizing said 5,6R,7,8-tetrahydrofolic acid or a salt or an ester thereof with other functional groups so as to form 5-substituted 5,6R,7,8-tetrahydrofolic acid or a salt or an ester thereof; and, if desired (c) converting the substantially pure 5-formyl5,6S,7,8-tetrahydrofolic acid or a salt or an ester thereof or 5-formyl-5,6R,7,8-tetrahydrofolic acid or a salt or an ester thereof to the corresponding acid, salt or ester.

The products of the process are valuable in their own right, for example, in therapy, and as intermediates to make other valuable products, and, when radiolabeled, they can be used to study enzymatic mechanisms, for example. Those skilled in this art will know how to use such compounds for such purposes.

Preferably, the process is used to make a desired, substantially pure 5-formyl-5,6S,7,8-tetrahydro-folic acid or a salt or ester thereof. Such compounds have valuable properties as rescue agents. Especially preferable is the process wherein the enzyme used for selectively formylating comprises tetrahydrofolate formylase. Also, the process is useful to make a desired substantially pure (6R or 6S) diastereoisomer of a derivative of (radiolabeled) tetrahydrofolic acid or a salt or ester thereof. Such materials can be used to study enzymatic mechanisms.

DETAILED DESCRIPTION OF THE INVENTION

The starting compounds used in this invention can be prepared by techniques well known to those skilled in the art of biochemical transformations. The mixtures of IIa(R) and IIb(S) can be prepared by sodium borohydride reduction of folic acid using the procedure of C. Temple, Jr., R. D. Elliot, J. D. Rose and J. A. Montgomery, J. Med. Chem., 22, 731 (1979).

Beginning with these materials, the reaction scheme of the invented process is as shown in Scheme I:

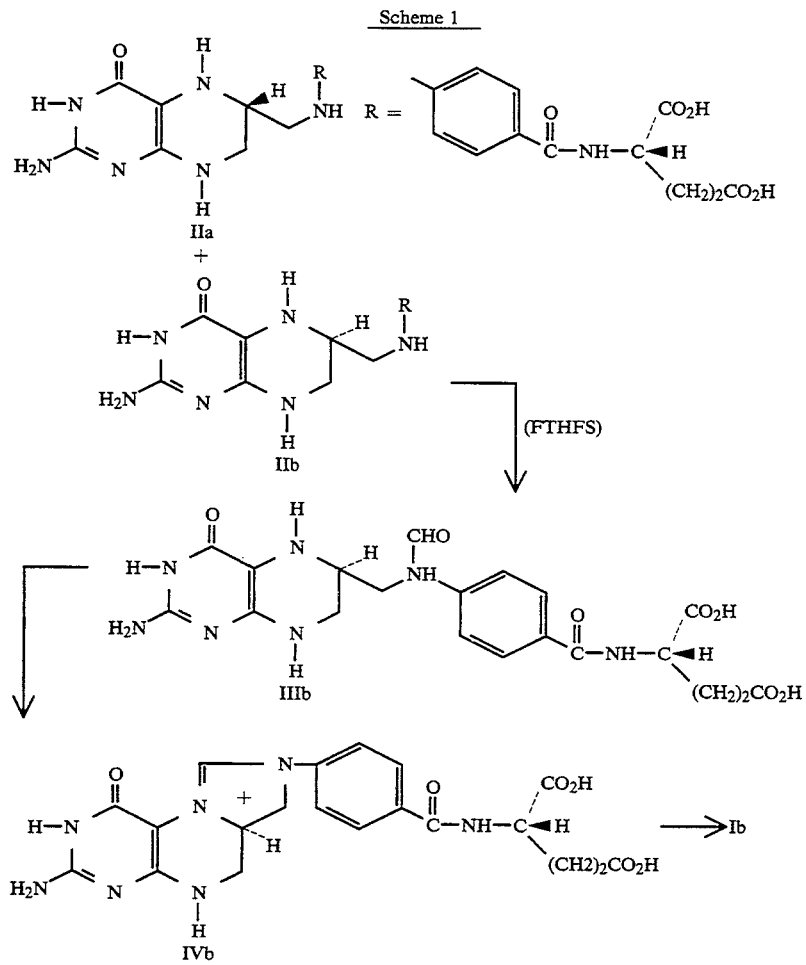

As shown in Scheme 2, (IIa) which can be separated from (IIIb) by chromatography is formylated with formic acid to give, under intermittent formation of (Ia), the imidazolinium salt (IVa) which after crystallization is hydrolyzed to afford the pure unnatural isomer of leucovorin (Ia). Alternatively, the mixture of (IIIb) and (IIa) can be carried on to convert (IIIb) to (IVb) and/or (Ib), thus producing a mixture of (IVb) and/or (Ib) and (IIa). Chromatography easily separates the components of the mixture, that is, (IIa) from (IVb).and/or (Ib).

This isolation procedure also constitutes a de facto separation of the 6R and 6S tetrahydrofolic acid diastereoisomers. Since (IIa) can be transformed to (Ia) chemically, this invention formally establishes a method for an effective separation of (Ib) from (Ia) which are more commonly referred to as the natural and non-natural forms of leucovorin.

Scheme 2

[Scheme 2: structure IIa converts to IVa then to Ia]

DESCRIPTION OF THE PREFERRED EMBODIMENTS

The following examples illustrate the invention but are not intended to limit the claims in any manner whatsoever.

PROCEDURE A

The isolation and growth of *Clostridium cylindrosporum* (also referred to as *Clostridium sp.* -ATCC No. 7905) is performed.

Since *Clostridium* is an anaerobe, all culture production, maintenance, and handling operations are carried out under conditions that minimized exposure of the strains to oxygen. Likewise, due to the extreme oxygen lability of tetrahydrofolate and its derivatives, all procedures involving these compounds are conducted in the absence of oxygen. A plastic anaerobic bag apparatus connected to an oxygen-free nitrogen gas source is used for this purpose.

1. Preparation of Uric Acid Growth Medium.

The uric acid medium is prepared as described in the ATCC Media Handbook-Recipe No. 519:

| Uric Acid Medium Composition | |
|---|---|
| Uric Acid | 3.0 g |
| Yeast Extract | 1.0 g |
| Potassium phosphate dibasic | 4.0 g |
| Magnesium sulfate heptahydrate | 0.1 g |
| Ferrous sulfate | 5.0 mg |
| *0.04% Phenol red solution | 1.0 g |
| Sodium-thioglycollate | 0.5 g |
| Distilled water | 1.0 L |

*14.9 ml 0.01 N sodium hydroxide required for 0.1 g indicator. Dilute to 250 ml with distilled water for 0.04% solution. In preparing the medium, the uric acid is suspended in almost the full volume of liquid, heated to boiling and adjusted to a permanent rose color of phenol red (pH 7.6) with sodium hydroxide. The pH is checked with pH paper. For solid medium 20.0 g of agar is added to the medium.

The medium is poured into a screw cap flask to nearly full volume then boiled while being purged with oxygen free nitrogen gas. Immediately following autoclaving the flask cap is screwed fairly tightly.

The medium is stored at room temperature to prevent uric acid precipitation at lower temperatures.

Inoculation of Growth Medium with *Clostridium Cylindrosporum* Culture

All procedures are carried out under anaerobic conditions in a glove bag. A 1.0 ml portion of the liquid uric acid medium is added to the lyophilized pellet of bacteria obtained from the ATCC. The pellet is dissolved and a sterile disposable inoculating loop is used to streak the resuspended culture on the uric acid plating medium. The plates are placed in an anaerobic jar containing an $H_2$—$CO_2$ generating envelope and a methylene blue indicator strip.

The jar containing the inoculated plates is incubated at 37° C. Within 24 hours growth is apparent on the plates as light, transparent, finger-like projections radiating from colonies. A sample of a representative colony as viewed under phase contrast microscopy reveals typical Clostridium cell morphology and spore formation.

3. Preparation of a permanent *Clostridium cylindrosporum* Stock Culture.

Uric acid plate medium is prepared in Hungate tubes (Bellco Glass Co.)—10 ml medium/tube and served as the source of a permanent Clostridium cylindrosporum stock culture. A single colony swatch of cells from a colony described above is picked with a sterile inoculating loop and stabbed into the Hungate tube medium. This procedure is carried out in an anaerobic bag containing nitrogen gas. The tubes are placed in the anaerobic jar and incubated at 35° C. After five days, the tubes are removed from the jar and the caps tightly sealed with parafilm. The tubes are stored at room temperature until further use.

4. Preparation of Liquid Growth Medium Inoculum

Tubes of semi-solid uric acid medium (2.5 g/1 Bacto-Agar) are inoculated with a colony of *Clostridium cylindrosporum*, incubated at 35° C. and stored at room temperature as noted above. These cultures serve as a source of inoculum for liquid medium growth as described in the following section.

5. Liquid Medium Growth of *Clostridium cylindrosporum*

One soft agar tube culture (entire 10 ml) is added to one liter of liquid uric acid medium. All operations are performed in an anaerobic bag and the entire culture is incubated in an anaerobic jar for 4 days at 35° C.

PROCEDURE B

Preparation of *Clostridium cylindrosporum* crude formyltetrahydrofolate synthetase extract is performed.

As in Procedure A, all culture production, maintenance and handling operations are carried out under conditions that minimize exposure of the strains to oxygen because Clostridium is an anaerobe. Likewise, due to the extreme oxygen lability of tetrahydrofolate and its derivatives, all procedures involving these compounds are conducted in the absence of oxygen. A plastic anaerobic bag apparatus connected to an oxygen-free nitrogen gas source is used for this purpose. The one liter culture becomes turbid and particulate material settles out of the medium. The culture is divided into 4×250 ml aliquots and added to 4×250 ml centrifuge bottles. The cultures are centrifuged at 4° C., 8,000 RPM, for 15 minutes in a Beckman J2-21 centrifuge.

Although the medium is chilled to 4° C., uric acid does not precipitate due to its consumption by the bacteria. The cell pellets are resuspended in 4×25 ml of ice-cold distilled water and centrifuged as above. The pellets are frozen at −20° C. for 5 days prior to being assayed for formyltetrahydrofolate synthetase.

The frozen pellets are thawed in a total of 4.0 ml of buffer (0.05M potassium biphosphate, 0.05M 2-mercaptoethanol (pH 7.5 by addition of 1M potassium hydroxide)). The pellets are mixed and allowed to dissolve by intermittent swirling at room temperature for 60 minutes. Noticeably the cell pellets become viscous due to cell lysis. Autolysis occurs at room temperature. The cell lysate is centrifuged at 17,000 RPM/30 minutes and the supernatant is retained on ice and assayed for formyltetrahydrofolate synthetase.

PROCEDURE C

Formyltetrahydrofolate Synthetase Assay is produced by the method provided in Buttlaire "Purification and Properties of Formyltetrahydrofolate Synthetase", Enzymology Vol. 66, p. 585, 1980).

EXAMPLE 1

Reduction of folic acid to 5,6(R,S),7,8-tetrahydrofolic acid is accomplished using a recent literature procedure (C. Temple, Jr., R. D. Elliott, J. D. Rose and J. A. Montgomery, J. Med. Chem. 22, 731 (1979)) employing sodium borohydride.

EXAMPLE 2

GENERATION OF 10-FORMYL-5,6S,7,8-TETRAHYDROFOLIC ACID

The following reaction mixture, suitable for the enzymatic formylation of 5,6S,7,8-tetrahydrofolic acid to produce 10-formyl-5,6S,7,8-tetrahydrofolic acid, is prepared: 100 ml of 1.0M triethanolamine hydrochloride (pH 8.0), 100 ml of 0.5M adenosine triphosphate (pH 8.0), 100 ml of 0.5M potassium chloride, 100 ml of 0.1M magnesium chloride hexahydrate, and 200 ml of 0.2M ammonium formate (pH 8.0). The content of an entire 5 g vial of 5,6(R,S),7,8-tetrahydrofolic acid (Sigma; 69 percent purity; Lot No. 117F-5013) is suspended in 200 ml 0.2M Tris-HCl/0.05M 2--mercaptoethanol (pH 7.0) and dissolved by the addition of approximately 15 ml of 1M potassium hydroxide. The clear solution is poured into the previous mixture and distilled water (approximately 200 ml) is added to make a total reaction mixture of 1.0 liter in a 2 liter glass bottle.

The reaction is started by adding 4 ml of the crude enzyme extract, containing "Formyltetrahydrofolate synthetase" (FTHFS) and allowing the reaction to proceed at room temperature (22° C). Samples are periodically removed to monitor the progress of the reaction by HPLC using a reverse-phase column {C-18) eluted with 0.1M formic acid and modified by methanol in a linear gradient from 12 to 25 percent over 30 minutes. The column eluate is monitored at 282 nm detecting 5,6(R,S),7,8-tetrahydrofolic acid at 12 minutes and 5,10-methenyl-tetrahydrofolic acid at 16 minutes. The reaction is completed after 18 hours. At this time, 48 percent of the original amount of 5,6(R,S),7,8-tetra-hydrofolic acid is left as determined by areas under the curve. An equivalent of 1585 mg of 10-formyl-5,6S,7,8-tetrahydrofolic acid from the reaction mixture is calculated from the HPLC chromatogram representing 5,10-methenyltetrahydrofolate. This accounts for a conversion of 92 percent of theory considering that only 1725 mg of the starting 3450 mg 5,6(R,S),7,8-tetrahydrofolic acid would be available for the enzymatic conversion reaction. Fifty percent of theory is converted after 5 hours.

EXAMPLE 3

CONVERSION OF 10-FORMYL-5,6S,7,8-TETRAHYDROFOLIC ACID TO 5-FORMYL-5,6S,7,8-TETRAHYDROFOLIC ACID

The reaction mixture from Example 2 is monitored for another day revealing no changes in its composition. A 100 ml portion of the mixture is transferred into a 3 neck bottle and the pH of the solution adjusted to 6.5 with sulfuric acid. While degassed with nitrogen, the bottle is immersed in a water bath and heated at 90°–95° C. for 2 hours. The reaction is then continued under nitrogen at 40° C. overnight. This reaction mixture has a brown appearance after 16 hours. A sample is analyzed by HPLC using a reverse-phase column (C-18) eluted with 0.1M formic acid and modified by methanol in a linear gradient from 12 to 25 percent over 30 minutes. The column eluate is monitored at 282 nm. The HPLC analysis indicates a conversion rate of 90.2 percent, when considering areas under the curve, for the peaks of 5,10-methenyl-5,6S,7,8-tetrahydrofolate and 5-formyl-5,6S,7,8-tetrahydrofolic acid. The area for the 5,6R,7,8-tetrahydrofolic acid, which should have been unchanged, is reduced to 33.1 percent relative to that of the starting material (48 percent).

Samples of the reaction mixture are added via a pump onto a preparative HPLC reverse-phase column (Dynamax 60A-C18, 8 micrometer, 2.1×30 cm) and then developed with a gradient of 0.1M aqueous formic acid and methanol at a flow rate of 13 ml/minute over 60 minutes. Somewhat yellow 5-formyl-5,6S,7,8-tetrahydro-folic acid is obtained in 82 percent overall yield, which under the acidic elution conditions (0.1M aqueous formic acid and methanol) is allowed to convert to 5,10-methenyl-5,6S,7,8-tetrahydrofolic acid which then on standing at a concentration of 3 to 6 mg/ml forms a gel in the collection vial. Enantiomeric purity of this sample was determined by HPLC using a chiral column (Diacel Chiracel OD), eluting isocratically with 0.5 percent ammonium formate, pH =3.8, and 25 percent methanol. A retention time of 15.2 minutes is recorded, with an optical rotation in formic acid as follows:

| Compound | Concentration (%) (88% formic acid solution) | Rotation (alpha D at 26° C.) |
| --- | --- | --- |
| 5,10-methenyl- | 0.611 | +42 |

| Compound | Concentration (%) (88% formic acid solution) | Rotation (alpha D at 26° C.) |
|---|---|---|
| 5,6S,7,8-tetra-hydrofolic acid | | |

EXAMPLE 4

CONVERSION OF 5,10-METHENYL--5,6S,7,8-TETRAHYDROFOLIC ACID TO 5-FORMYL-5,6S,7,8-TETRAHYDROFOLIC ACID AND 5,6R,7,8-TETRAHYDROFOLIC ACID

The pH of the rest of the reaction mixture as obtained from Example 2 is adjusted from 8.0 to 5.0 with sulfuric acid, initiating a rapid cyclization of 10-formyl-5,6S,7,8-tetrahydrofolic acid to 5,10-methenyl5,6S,7,8-tetrahydrofolic acid which then on standing at room temperature slowly hydrolyzes to form 5-formyl-5,6S, 7,8-tetrahydrofolic acid. The latter is not detected in the reaction mixture prior to the pH adjustment.

The reaction is followed by HPLC using a reverse-phase column (C-18) eluted with 0.1M formic acid and modified by methanol in a linear gradient from 12 to 25 percent over 30 minutes. Monitoring the reaction by HPLC reveals that more than 70 percent of the original 5,10-methenyl-5 ,6S,7,8-tetrahydrofolic acid was converted to 5- formyl-5,6S,7,8-tetrahydrofolic acid after 5 days at room temperature during which time the concentration o f 5,6R,7,8-tetrahydrofolic acid in the reaction mixture remains unchanged. The formylated products, obtained as 5-formyl-5,6S,7,8-tetrahydrofolic acid and 5, 10-methenyl-5,6S ,7,8-tetrahydrofolic acid, and the unformylated 5,6R,7 ,8-tetrahydrofolic acid, are then isolated by preparative HPLC reverse-phase column (Dynamax 60 A-C18, 8 micrometer, 2.1×30 cm), developed with a gradient of 0.1M aqueous formic acid and methanol at a flow rate of 13 ml/minute over 60 minutes. Determined yields of two preparations (each equivalent to 50 ml re action mixtures) are as follows:

| Isolated Compound (mg) | Yield (%) | Rel. Yield |
|---|---|---|
| 5,10-methenyl-5,6S,7,8-tetra-hydrofolic acid (22.6) | 12.9 | 6.5 |
| 5-formyl-5,6S,7,8-tetrahydro-folic acid (118.2) | 67.5 | 33.8 |
| 5,6R,7,8-tetrahydrofolic acid* (145.5) | 83.1 | 41.6 |

*The isolated 5,6R,7,8-tetrahydrofolic acid is immediately dried and formylated with formic acid (as described below) to obtain 5,10-methenyl-5,6R,7,8-tetrahydrofolic acid, which, unlike the 6S form, crystallizes out of dilute formic acid.

EXAMPLE 5

FORMYLATION OF 5,6R,7,8-TETRAHYDROFOLIC ACID TO YIELD CRYSTALLINE 5,10-METHENYL-5,6R,7,8-TETRAHYDROFOLIC ACID

A 253 mg sample of chromatographically purified and lyophilized 5,6R,7,8-tetrahydrofolic acid is dissolved in 50 ml of 97 percent formic acid containing 2 percent trifluoroacetic acid and left at ambient temperature in the reaction bottle under nitrogen without stirring. The reaction is analyzed by HPLC using a reverse-phase column (C-18) eluted with 0.1M aqueous formic acid and modified by methanol in a linear gradient from 12 to 25 percent over 30 minutes and monitored at 282 nm. After three hours all of the 5,6R,7,8-tetrahydrofolic acid has reacted as judged by the appearance of a new peak representing 5,10-methenyl5,6R,7,8-tetrahydrofolic acid in the HPLC chromatogram. The bulk of the formic acid is consequently removed by evaporation and 30 ml of 0.1M aqueous formic acid was slowly added with occasional swirling of the mixture. The solution is then stored in the chill room overnight. Tiny yellow needles form, giving the solution the appearance of a solid. The crystals are collected on a glass-fritted funnel, washed with acetone, and dried in vacuum yielding 218 mg of yellow crystalline material.

The enantiomeric purity of crystalline 5,10-methenyl-5,6R,7,8-tetrahydrofolic acid is determined using a chira column (Diacel Chiracel OD) eluted isocratically with 0.5 percent ammonium formate, pH 3.8 and 25 percent methanol. The product, 5,10-methenyl-5,6R,7,8-tetrahydrofolic acid, eluted at 18.2 minutes.

The optical rotation, determined as solution in 88 percent formic acid, is as follows:

| Compound | Concentration (%) (88% formic acid solution) | Rotation (alpha D at 26° C.) |
|---|---|---|
| 5,10-methenyl-5,6R,7,8-tetra-hydrofolic acid | 0.619 | −47 |

EXAMPLE 6

DERIVATIZATION OF 5,6R,7,8-TETRAHYDROFOLIC ACID IN TEE PRESENCE OF 5-FORMYL-5,6S,7,8-TETRAHYDROFOLIC ACID AND/OR 5,10-METHENYL-5,6S,7,8-TETRAHYDROFOLIC ACID

Modifying the procedure set forth by L. Rees, C. J. Suckling and H. C. S. Wood, J. Chem. Soc. Chem. Commun. 470 (1987), (-)menthylchloroformate is added to a sample of the reaction mixture from Example 4, adjusted to pH 7, which results in the carboxymenthylation of only 5,6R,7,8-tetrahydrofolic acid and leaves 5-formyl5,6S,7,8-tetrahydrofolic acid and/or 5,10-methenyl-5,6S, 7,8-tetrahydrofolic acid unreacted. The reaction was monitored Dy HPLC. An effective separation of 5-menthyl-oxycarbonyl-5,6R,7,8-tetrahydrofolic acid from the unreacted components is accomplished by passing the reaction mixture over an XAD-2 loaded column. The 5-menthyloxycarbonyl--5,6R,7,8--tetrahydrofolic acid is absorbed by the resin and the 5-formyl--5,6S,7,8--tetra-hydrofolic acid or 5,10-methenyl-5,6S,7,8-tetrahydrofolic acid passes through.

EXAMPLE 7

PURIFICATION OF 5-FORMYL-5,6S,7,8-TETRAHYDROFOLIC ACID, 5,6R,7,8-TETRAHYDROFOLIC ACID AND OTHER DERIVATIVES BY PREPARATIVE APLC

Portions (50 or 100 ml) of the reaction mixture from Example 4 are loaded directly onto the reverse-phase column (Dynamax 60A-C18, 8 micrometer, 2.1 ×30 cm) through a loading pump and then developed with a gradient of 0.1M aqueous formic acid and methanol at a flow rate of 13 ml/minute over 60 minutes. The gradient used starts with a methanol concentration of 5 percent to reach 10 percent after 12 minutes run time. The concentration of 10 percent methanol is then kept constant for the next 10 minutes at which time (22 minutes into run) the level of methanol is linearly increased to reach 18 percent by 38 minutes and from there increased further to reach 25 percent at 52 minutes run time. This concentration is not further increased until the end of the run. The column effluent is monitored at 319 nm because 5,10-methenyl-5,6S,7,8-tetrahydrofolate and 5-formyl-5,6S,7,8-tetrahydrofolic acid have the same absorption coefficient at that wavelength.

Under these preparative conditions 5,6R,7,8-tetrahydrofolic acid eluted between 11 and 17.5 minutes, whereas the 5-formyl-5,6S,7,8--tetrahydrofolic acid eluted between 39.5 and 44.5 minutes. The elution of the 5,10-methenyl-5,6S,7,8--tetrahydrofolate band is strongly concentration dependent appearing between 20 and 30 minutes as a trailing peak. The 5,6R,7,8-tetrahydrofolic acid band and the 5,10-methenyl-5,6S,7,8-tetrahydrofolate band cannot be completely separatea when more than 140 ml of the reaction mixture, equivalent to 700 mg of material is loaded.

Eluting bands of 5,6R,7,8-tetrahydrofolic acid and 5-formyl--5,6S,7,8--tetrahydrofolic acid are collected into glass bottles which are immersed in dry ice so that the liquid can freeze immediately. The frozen fractions are then lyophilized to yield a grayish-white powder in the case of 5,6R,7,8-tetrahydro-folic acid, and a yellowish-white powder in the case of 5-formyl-5,6S,7,8-tetrahydrofolic acid. HPLC analysis is performed on these powders using a reverse-phase column (Dynamax 60A-C18, 8 micrometer, 2.1×30 cm) developed with a gradient of 0.1M aqueous formic acid and methanol. The 5-formyl--5,6S,7,S-tetrahydrofolic acid is shown to be 97 percent and 5,6R,7,8-tetrahydro-folic acid 93 percent pure by area under the curve. Because of the instability of 5,6R,7,8-tetrahydrofolic acid, it is converted by chemical formylation to the more stable 5,10-methenyl-5,6R,7,8--tetrahydrofolic acid. To counteract any stability problem of 5-formyl-5,6S,7,8-tetrahydrofolic acid, this compound is converted to its calcium salt as described in Example 8.

EXAMPLE 8

PREPARATION OF CALCIUM 5-FORMYL--5,6S,7,8-TETRAHYDROFOLATE OR CALCIUM 5-FORMYL-5,6R,7,8-TETRAHYDROFOLATE

In modification of the procedure published by C. Temple, Jr., R. D. Elliott, J. D. Rose and J. A. Montgomery, J. Med. Chem., 22, 731 (1979) to produce racemic calcium 5-formyl--5,6(R,S),7,8--tetrahydrofolate, prepared 5-formyl-5,6S,7,8-tetrahydrofolic acid is washed with ether to remove possible ammonium formate. Sixty-two mg of the washed material is then dissolved in 32 ml degassed methanol (salt-free folinic acid is well soluble in methanol) to which about 1 ml of a methanolic calcium chloride solution (72 mg calcium chloride per ml methanol) is added. The addition of the salt causes the immediate formation of an off-white precipitate which is collected on a glass-fritted funnel and dried in vacuum. The yield after drying is 60.5 mg (90 percent of theoretical yield.).

If this process is repeated with 6R materials, there will be obtained calcium 5-formyl-5,6R,7,8-tetrahydrofolate.

The purity of the prepared compounds is determined by UV/HPLC disregarding the presence of any non-UV-absorbing matter. Enantiomeric purity is determined at the stage of the 5,10-methenyl-5,6(R,S),7,8-tetrahydrofolate derivatives by HPLC using a chiral column (Diacel Chiracel OD) eluted isocratically with .0.5 percent ammonium formate pH 3.8 and 25 percent methanol. 5,10-Methenyl-5,6S,7,8-tetrahydrofolic acid elutes first with 15.2 minutes retention whereas 5,10-methenyl5,6R,7,8-tetrahydrofolic acid elutes at 18.2 minutes.

Solutions of the prepared compounds in formic acid rather than 10M or 12M hydrochloric acid, as reported in the literature, were used to record their optical rotation properties, because of the reduced acidity of formic acid and its increased dissolving power for folates. Samples of the above preparations showed the following optical rotations:

| Compound | Concentration (%) (88% formic acid solution) | Rotation (alpha D at 26° C.) |
|---|---|---|
| 5,10-methenyl-5,6S,7,8-tetrahydrofolic acid* | 0.611 | +42 |
| 5,10-methenyl-5,6R,7,8-tetrahydrofolic acid** | 0.619 | −47 |

*Chromatographically isolated as 5-formyl-5,6S,7,8-tetrahydrofolic acid, which on standing in the eluted 0.1 M formic acid mixture converted to 5,10-methenyl-5,6S,7,8-tetrahydrofolic acid and then solidified to form a gel which was lyophilized.
**Originally isolated as non-converted 5,6R,7,8-tetra-hydrofolic acid, which after lyophilization was immediately formylated with formic acid as described previously. The resulting 5,10-methenyl-5,6R,7,8-tetrahydrofolic acid which crystallized out of a diluted formic acid mixture is collected, washed with acetone, and dried in vacuum. Of 253 mg 5,6R,7,8-tetrahydrofolic acid (by weight), 218 mg of crystalline 5,10-methenyl-5,6R,7,8-tetrahydrofolic acid (by weight) is collected.

EXAMPLE 9

PREPARATION OF RADIOLABELED FORMYLFOLIC ACID AND DERIVATIVES

If the procedure of Example 2 is repeated by substituting ammonium formate with radiolabeled ammonium formate or any other radiolabeled formic acid derivative, there will be obtained a radiolabeled 10-formyl-5,6S,7,8-tetrahydrofolic acid. If this is subjected to the procedures of Examples 3–8, inclusively, the corresponding radiolabeled acids and salts will be obtained.

The above-mentioned patents, publications and test methods are incorporated herein by reference.

The foregoing detailed description will suggest many obvious variations to those skilled in this art. For example, instead of calcium leucovorin, strontium leucovorin and sodium leucovorin can be produced. The tetrahydrofolate formylase can be elaborated by Clostridium acidi-urici. All such obvious modifications are within the full intended scope of the appended claims.

We claim:

1. A process for preparing a substantially pure calcium salt of 5-formyl-5, 6S,7,8-tetrahydrofolic acid, which process comprises the steps of:
   (a) enzymatically formylating the 6S form of a mixture of 6R and 6S diastereoisomers of 5,6,7,8-tetrahydrofolic acid utilizing a tetrahydrofolate formylase enzyme elaborated by Clostridium sp. ATCC No. 7905 or a mutant thereof so as to form a mixture comprising 10-formyl-5,6S,7,8-tetrahydrofolic acid; unreacted 5,6S,7,8-tetrahydrofolic acid and unreacted 5,6R,7,8-tetrahydrofolic acid;

(b) cyclizing said 10-formyl-5,6S, 7,8-tetrahydrofolic acid form 5,10-methenyl-5,6S, 7,8-tetra hydrofolic acid and hydrolyzing and 5,10-methenyl-5,6S,7,8-tetrahydrofolic acid to form 5-formyl-5,6S, 7,8-tetrahydrofolic acid, wherein said cyclizing and hydrolyzihng steps are conducted in the presence of 5,6R,7,8-tetrahydrofolic acid;

(c) separating the 5-formyl-5,6S, 7,8-tetrahydrofolic acid form 5,10-methenyl-5,6S, 7,8-tetra hydrofolic acid and 5,6R, 7,8-tetrahydrofolic acid by reverse phase chromatographic separation, and developed with a gradient of 0.1M aqueous formic acid and methanol;

(d) converting the substantially pure 5-formyl-5,6-S,7,8-tetrahydrofolic acid to the corresponding calcium salt using calcium chloride or a chemical equivalent thereof.

* * * * *